United States Patent [19]

Brooks

[11] Patent Number: 4,810,700

[45] Date of Patent: Mar. 7, 1989

[54] COMPOSITIONS INHIBITING ESTROGEN SULFOTRANSFERASE ACTIVITY

[75] Inventor: Samuel C. Brooks, West Bloomfield, Mich.

[73] Assignee: Wayne State University, Detroit, Mich.

[21] Appl. No.: 495,221

[22] Filed: May 18, 1983

Related U.S. Application Data

[63] Continuation of Ser. No. 355,806, Mar. 8, 1982, abandoned, which is a continuation-in-part of Ser. No. 952,592, Oct. 18, 1978, Pat. No. 4,340,602.

[51] Int. Cl.⁴ .............................................. A61K 31/56
[52] U.S. Cl. ..................................... 514/178; 514/843
[58] Field of Search ......................... 424/238; 514/178

[56] References Cited

PUBLICATIONS

Utne et al., "Journal of Organic Chemistry", Jun. (1968), pp. 2469-2473.

Primary Examiner—Leonard Schenkman
Assistant Examiner—Joseph A. Lipovsky
Attorney, Agent, or Firm—Sidney B. Williams, Jr.

[57] ABSTRACT

An estrogen sulfotransferase inhibitor composition comprises a compound of the formula

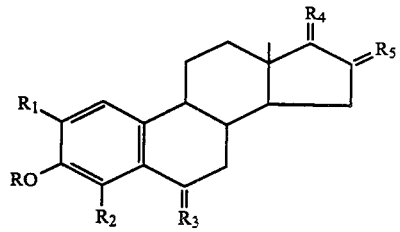

wherein $R_1$ is F, Br, $NO_2$, or H; $R_2$ is F, Br, $NO_2$, $NH_2$, or H; R is H or alkyl of 1-4 carbon atoms; $R_3$ is O or $H_2$; and $R_4$ is $H_2$, O, or $\alpha$-H, $\beta$-OH; $R_5$ is $H_2$, $\alpha$-H and $\beta$-OH or B-H and $\alpha$-OH in admixture with a pharmaceutically acceptable carrier with the proviso that $R_1$, $R_2$ and $R_3$ cannot all be hydrogen and one of $R_1$ and $R_2$ is F.

2 Claims, No Drawings

COMPOSITIONS INHIBITING ESTROGEN SULFOTRANSFERASE ACTIVITY

This invention described herein was made in the course of work under a Public Health Service Grant No. HD 14775-01 from the Department of Health, Education and Welfare.

CROSS REFERENCE TO RELATED APPLICATION

This is a continuation of application Ser. No. 355,806 filed Mar. 8, 1982 now abandoned, which is a continuation-in-part of copending application Ser. No. 952,592, filed Oct. 18, 1978, now U.S. Pat. No. 4,340,602.

BRIEF SUMMARY OF THE INVENTION

The present application relates to novel estrogen sulfotransferase inhibitor compositions and their method of use. In particular, the present invention relates to the novel estrogen sulfotransferase inhibitor compositions and method of use disclosed in U.S. Ser. No. 952,592, now U.S. Pat. No. 4,340,602 the disclosure of which is incorporated here by reference.

In particular, U.S. Ser. No. 952,592, now U.S. Pat. No. 4,340,602 describes the use of certain estrogen sulfotransferase inhibitor compositions and methods of use. With respect to the specification of U.S. Ser. No. 952,592, now U.S. Pat. No. 4,340,602 particular reference is made to Tables I and II. Table I gives inhibition constants and fraction inhibition as a function of the oxygenated substituents at the 3' and 17$\beta$' positions of estrogens. Table II gives the same data for substituted estrogen analogs.

Moreover, the Examples 2, 3, and 4 provide essential characteristics of this invention. Examples 5, 6, 7, and 8 describes particular compositions for use as estrogen sulfotransferase inhibiting preparations.

Accordingly, there are described in the "Summary of the Invention" in U.S. Ser. No. 952,592, now U.S. Pat. No. 4,340,602 an estrogen sulfotransferase inhibitor composition comprising a compound of the formula which is expanded but then also limited to more nearly reflect the scope of the disclosed invention in the claims of U.S. Ser. No. 952,592, now U.S. Pat. No. 4,340,602 having an $R_5$ substituent added, as well as, having a proviso in which $R_1$, $R_2$, and $R_3$ can not all be hydrogen as follows:

A composition wherein the estrogen sufotransferase inhibiting compound is a compound selected from the group consisting of the formula

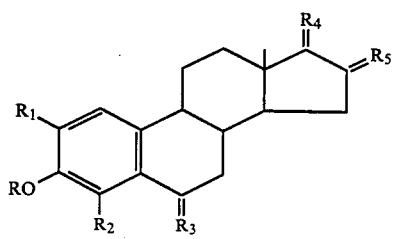

wherein $R_1$ is Br, $NO_2$ or H; $R_2$ is Br, $NO_2$, $NH_2$, or H; R is H or alkyl of 1-4 carbon atoms, inclusive; $R_3$ is O or $H_2$; and $R_4$ is $H_2$, O or $\alpha$-H, $\beta$-OH; $R_5$ is $H_2$, $\alpha$-H, $\beta$-OH or $\beta$-H, $\alpha$-OH in admixture with a pharmaceutically acceptable carrier with the proviso that $R_1$, $R_2$, and $R_3$ cannot all be hydrogen.

Likewise, certain additional estrogen sulfotransferase inhibiting compounds represent novel compositions comprising one aspect of the present invention. These generally comprise compounds wherein one of $R_1$ or $R_2$ is F.

Preferred compounds for the practice of the invention as found in U.S. application Ser. No. 952,592 are those wherein:
(a) R is methyl;
(b) $R_1$ is H, including (a);
(c) $R_1$ is Br, $NO_2$ or $NH_2$, including (a);
(d) $R_2$ is Br, including each of (a)-(c);
(e) $R_2$ is $NO_2$, including each of (a)-(c);
(f) $R_2$ is $NH_2$, including each of (a)-(c);
(g) $R_3$ is O, including each of (a)-(f);
(h) $R_3$ is $H_2$, including each of (a)-(f);
(i) $R_4$ is O, including each of (a)-(h); and
(j) $R_4$ is $\alpha$-H, $\beta$-OH, including each of (a)-(h).

In addition certain prepared compounds for estrogen sulfotransferase inhibition are preferred comprising one aspect of the present invention which while limited to one of $R_1$ or $R_2$ as F are also as follows: (b), (c), (d), (e), (f), (g), (h), (i), and (j) as outlined above are expanded to include:
(b) $R_1$ is F or H, including (a);
(c) $R_1$ is F, Br, $NO_2$ or $NH_2$, including (a);
(d) $R_2$ is F, Br, including each of (a)-(c) as expanded herein;
(e) $R_2$ is F or $NO_2$, including each of (a)-(c) as expanded herein;
(f) including each of (a)-(c) as expanded herein;
(g) and (h) each including (a)-(f) as expanded herein;
(i) and (j) each including (a)-(h) as expanded herein;

Particularly preferred compounds as found in U.S. Ser. No. 952,592 are those wherein:
(a) R is methyl, $R_2$ is $NO_2$ and $R_3$ is O;
(b) R is methyl, $R_1$ and $R_2$ both are Br or $NO_2$ and $R_4$ is O or $\alpha$-H, $\beta$-OH;
(c) R is methyl, $R_1$ is H, and $R_2$ is $NH_2$;
(d) R is methyl, and $R_4$ is $\alpha$-H, $\beta$-OH;
(e) $R_1$ and $R_2$ are $NO_2$;
(f) $R_1$ and $R_2$ are Br;
(g) R is methyl, $R_1$ is H, and $R_4$ is $\alpha$-H, $\beta$-OH.

Particularly preferred compounds, therefore, in addition to those enumerated above now also include:
(h) R is methyl, and one of $R_1$ or $R_2$ is F.

Finally, most preferred in addition to those named above from U.S. application Ser. No. 952,592, now U.S. Pat. No. 4,340,602 now also include as the present invention 2-fluoroestrone-3-methyl ether and 4-fluoroestrone-3-methyl ether.

Moreover, the fluoro containing estrogen sufotransferase inhibiting compounds of the present invention are used by following procedures similar to those of Examples 1 through 4 and in compositions similar to Examples 5 through 8 or as fully disclosed in U.S. application Ser. No. 952,592, now U.S. Pat. No. 4,340,602.

Therefore, the present invention now comprises the discovery that fluoro containing sulfotransferase inhibitors and particularly 2-fluoro and 4-fluoroestrone-3-methyl ether comprises one aspect of the present invention. The 2-fluoro and 4-fluoroestrone-3-methyl ether are prepared by a process disclosed by Filler, "Reactions of Organic Compounds with Xenone Fluorides, *Israel Journal of Chemistry*, Vol. 16, pp. 71–79, (1978). Compositions for and method of using these compounds in the present invention are fully disclosed in the above discussion.

I claim:

1. A unit dosage pharmaceutical composition for the prevention of implanation of a blastocyst in the epithelial uterine lining of a female mammal and possessing a total per unit dosage of an accurate predetermined amount of an estrogen sulfotransferase inhibiting compound such that said dosage is administered daily for from 3 to 9 days in quantities each day of from 0.1 to 500 mg of the compound, wherein the compound is 4-fluoroestrone-3-methyl ether.

2. A method of treating a female mammal to prevent implanation of a blastocyst which method comprises administering an effective dosage of an estrogen sulfotransferase inhibiting compound wherein the compound is 4-fluoroestrone-3-methyl ether.

* * * * *